(12) United States Patent
Wang et al.

(10) Patent No.: US 11,071,862 B2
(45) Date of Patent: Jul. 27, 2021

(54) NONINVASIVE DEEP BRAIN STIMULATION SYSTEM HAVING K FOCUSES

(71) Applicant: Xi'an Jiaotong University, Xi'an (CN)

(72) Inventors: Jue Wang, Xi'an (CN); Xiaoqi Zhu, Xi'an (CN); Zi-Gang Huang, Xi'an (CN); Youjun Li, Xi'an (CN); Liang Zheng, Xi'an (CN); Tian Liu, Xi'an (CN); Bixin Shao, Xi'an (CN); Chenxi Li, Xi'an (CN); Xun Liu, Xi'an (CN); Ziwei Xu, Xi'an (CN); Boya Xu, Xi'an (CN)

(73) Assignee: XI'AN JIAOTONG UNIVERSITY, Xi'an (CN)

( * ) Notice: Subject to any disclaimer, the term of this patent is extended or adjusted under 35 U.S.C. 154(b) by 161 days.

(21) Appl. No.: 16/228,090

(22) Filed: Dec. 20, 2018

(65) Prior Publication Data

US 2019/0366088 A1 Dec. 5, 2019

(30) Foreign Application Priority Data

May 29, 2018 (CN) .......................... 201810571695.7

(51) Int. Cl.
*A61N 1/36* (2006.01)
*A61B 5/00* (2006.01)
(Continued)

(52) U.S. Cl.
CPC ....... *A61N 1/36025* (2013.01); *A61N 1/3603* (2017.08); *A61B 5/4064* (2013.01); *A61N 1/0456* (2013.01); *A61N 1/0529* (2013.01)

(58) Field of Classification Search
CPC .... A61N 1/36; A61N 1/36025; A61N 1/3603; A61N 1/4064; A61N 1/0456; A61N 1/0529; A61B 5/4064
See application file for complete search history.

(56) References Cited

U.S. PATENT DOCUMENTS

| | | | | |
|---|---|---|---|---|
| 6,815,694 B2 * | 11/2004 | Sfez | ..................... | A61B 5/0073 250/492.1 |
| 7,174,213 B2 * | 2/2007 | Pless | .................. | A61N 1/36064 607/45 |

(Continued)

*Primary Examiner* — Christopher A Flory
(74) *Attorney, Agent, or Firm* — Dragon Sun Law Firm, PC; Jinggao Li, Esq.

(57) ABSTRACT

There is provided a deep brain stimulation system having k focuses, which comprises: a first electrode and a second electrode, used for connecting one side of a brain scalp; a third electrode and a fourth electrode, used for connecting the other side of the brain scalp; and a first signal generation unit, a second signal generation unit, . . . , a $(2k-1)^{th}$ signal generation unit and a $2k^{th}$ signal generation unit, wherein the k is a positive integer greater than or equal to 2; and each of the signal generation units is used for providing the following currents for the first electrode to the fourth electrode: a first current and a second current, which are interfered at a deep portion of a brain to form a first focus; and a $(2k-1)^{th}$ current and a $2k^{th}$ current, which are interfered at the deep portion of the brain to form a $k^{th}$ focus.

12 Claims, 4 Drawing Sheets

(51) Int. Cl.
*A61N 1/04* (2006.01)
*A61N 1/05* (2006.01)

(56) References Cited

U.S. PATENT DOCUMENTS

| | | | |
|---|---|---|---|
| 9,339,642 B1* | 5/2016 | Bikson | A61N 1/0476 |
| 2005/0187591 A1* | 8/2005 | Carter | A61N 1/32 |
| | | | 607/46 |
| 2007/0004984 A1* | 1/2007 | Crum | A61B 8/06 |
| | | | 600/471 |
| 2008/0021490 A1* | 1/2008 | Briggs | A61B 5/150152 |
| | | | 606/181 |
| 2013/0317325 A1* | 11/2013 | Wood | A61B 5/14551 |
| | | | 600/310 |
| 2013/0345774 A1* | 12/2013 | Paulus | A61N 1/36034 |
| | | | 607/45 |
| 2015/0148863 A1* | 5/2015 | Yun | A61B 5/6868 |
| | | | 607/45 |
| 2015/0174418 A1* | 6/2015 | Tyler | A61B 34/10 |
| | | | 601/2 |
| 2017/0291044 A1* | 10/2017 | Zheng | A61B 5/0484 |

* cited by examiner

NONINVASIVE DEEP BRAIN STIMULATION SYSTEM HAVING K FOCUSES

CROSS REFERENCE TO RELATED APPLICATION

This application is based upon and claims priority to Chinese Patent Application No. 201810571695.7, filed on May 29, 2018, the entire content of which is incorporated herein by reference.

TECHNICAL FIELD

The present disclosure relates to the medical field, and particularly relates to a deep brain stimulation system having k focuses.

BACKGROUND

In a working loop formed by multiple brain areas in a brain functional network, the multiple brain areas need to work simultaneously and cooperatively, so that a certain functional effect can be generated, e.g., a cortex-thalamus-cortex loop assists cortex function recombination after stroke. Hence, the multiple brain areas are stimulated simultaneously in a targeted manner to activate a specific neural loop, which is of great significance for implementation of a certain functional effect of the brain.

However, the existing nerve electrical stimulation technology has many limitations, e.g., transcranial direct-current stimulation (tDCS) and transcranial alternating-current stimulation (tACS) only can implement diffuse stimulation, stimulate the whole brain simultaneously and have no tendency and targeting. Implantable deep brain stimulation has a surgical risk and an implanted electrode has a negative effect on a brain function (e.g., recognition) of a patient.

A noninvasive deep brain stimulation technology is a technology in which high and different frequency (the difference is $\Delta f$) sinusoidal stimulation currents mediated by 4 transcranial electrodes (constituting 2 channel currents) are interfered at a deep brain area to generate a low-frequency enveloped stimulation electric field to stimulate the deep brain. Due to no high-frequency responsiveness of a neural cell, a high-frequency stimulation current does not generate a stimulation effect when passing through the brain cortex and only the interference low-frequency enveloped stimulation electric field at the deep brain generates the stimulation effect, and thus a function of stimulating the deep brain is achieved by using a noninvasive transcranial method.

The deep brain stimulation provided by existing patents is invasive implantable stimulation and thus brings a great inconvenience to clinical application, e.g., the deep brain stimulation apparatus introduced by the Patent with the Publication No. 201080033903.X needs to implant a stimulation electrode into the brain of the patient to implement the deep stimulation and has the defect of invasion. The researches on the noninvasive deep brain stimulation stays in single-focus targeted stimulation, and the researches on the noninvasive deep brain stimulation that simultaneously activating dual (multiple) target brain areas in a targeted manner to form dual (multiple) focuses remain unexplored.

SUMMARY

In order to solve the above-mentioned technical problems, the present disclosure discloses a deep brain stimulation system having k focuses, which includes:

a first electrode and a second electrode, used for connecting one side of a brain scalp;
a third electrode and a fourth electrode, used for connecting the other side of the brain scalp; and
a first signal generation unit, a second signal generation unit, . . . , a $(2k-1)^{th}$ signal generation unit and a $2k^{th}$ signal generation unit, wherein the k is a positive integer greater than or equal to 2;
the first signal generation unit is used for outputting a 1_1 current for the first electrode and a 1_2 current for the second electrode, wherein the frequency of each of the 1_1 current and the 1_2 current is a first frequency value, the phase difference between the 1_1 current and the 1_2 current is 180° and the 1_1 current and the 1_2 current both are recorded as a first current;
the second signal generation unit is used for outputting a 2_1 current for the third electrode and a 2_2 current for the fourth electrode, wherein the frequency of each of the 2_1 current and the 2_2 current is a second frequency value, the phase difference between the 2_1 current and the 2_2 current is 180° and the 2_1 current and the 2_2 current both are recorded as a second current;
the $(2k-1)^{th}$ signal generation unit is used for outputting a 2k-1_1 current for the first electrode and a 2k-1_2 current for the second electrode, wherein the frequency of each of the 2k-1_1 current and the 2k-1_2 current is a $(2k-1)^{th}$ frequency value, the phase difference between the 2k-1_1 current and the 2k-1_2 current is 180° and the 2k-1_1 current and the 2k-1_2 current both are recorded as a $(2k-1)^{th}$ current;
the $2k^{th}$ signal generation unit is used for outputting a 2k_1 current for the third electrode and a 2k_2 current for the fourth electrode, wherein the frequency of each of the 2k_1 current and the 2k_2 current is a $2k^{th}$ frequency value, the phase difference between the 2k_1 current and the 2k_2 current is 180° and the 2k_1 current and the 2k_2 current both are recorded as a $2k^{th}$ current;
the first frequency value, the second frequency value, the $(2k-1)^{th}$ frequency value and the $2k^{th}$ frequency value all are greater than 1 kHz and are different from one another;
and the difference between two frequency values of the first frequency value and the second frequency value, . . . , the $(2k-1)^{th}$ frequency value and the $2k^{th}$ frequency value is greater than 1 Hz and is smaller than 100 Hz;
the first current and the second current are interfered at a deep portion of a brain to form a first focus, and the $(2k-1)^{th}$ current and the $2k^{th}$ current are interfered at the deep portion of the brain to form a $k^{th}$ focus;
for the first current, the second current, . . . , the $(2k-1)^{th}$ current and the $2k^{th}$ current, each of the currents is a sine wave of which the peak-to-peak value is unchanged all the time; and
from the first focus to the $k^{th}$ focus, the interference of the currents is not occurred therebetween.

Through the above-mentioned technical solution, the deep brain stimulation system can perform stimulation of two focuses or more on the drain deep portion, and can be used in simulation research or a therapeutic field; and when being used in the therapeutic field, the deep brain stimulation system has the characteristic of non-invasion.

1—system display screen; 2—parameter setting buttons; 3—system power buttons; 4—electrode output interfaces; 5—extended connection interface.

DETAILED DESCRIPTION

In order to make a person skilled in the art understand the technical solution of the present disclosure, technical solution of each embodiment will be described below in combination with the embodiments and related accompanying drawings. The embodiments described below are a part, but not all, of the embodiments of the present disclosure. As used herein, the terms "first", "second", and the like are intended to distinguish different objects rather than describe a specific order or sequence. In addition, the terms "include", "have" and any other variants mean to cover the non-exclusive inclusion, e.g., a process, or a method, or a system, or a product or a device that includes a series of steps or units is not limited to the listed steps or units, but optionally further includes steps or units not listed, or optionally further includes other steps or units inherent to such a process, method, product, or device.

Reference in this specification to "one embodiment" or "an embodiment" means that a particular feature, structure, or characteristic described in connection with the embodiment is included in at least one embodiment of the present disclosure. The appearances of the phrase in various places in the specification are not necessarily all referring to the same embodiment, nor are separate or alternative embodiments mutually exclusive of other embodiments. It may be understood by the person skilled in the art that the described embodiments may be combined with other embodiments.

In an embodiment, the present disclosure discloses a deep brain stimulation system having k focuses, which includes:
  a first electrode and a second electrode, used for connecting one side of a brain scalp;
  a third electrode and a fourth electrode, used for connecting the other side of the brain scalp; and
  a first signal generation unit, a second signal generation unit, . . . , a $(2k-1)^{th}$ signal generation unit and a $2k^{th}$ signal generation unit, wherein the k is a positive integer greater than or equal to 2;
  the first signal generation unit is used for outputting a 1_1 current for the first electrode and a 1_2 current for the second electrode, wherein the frequency of each of the 1_1 current and the 1_2 current is a first frequency value, the phase difference between the 1_1 current and the 1_2 current is 180° and the 1_1 current and the 1_2 current both are recorded as a first current;
  the second signal generation unit is used for outputting a 2_1 current for the third electrode and a 2_2 current for the fourth electrode, wherein the frequency of each of the 2_1 current and the 2_2 current is a second frequency value, the phase difference between the 2_1 current and the 2_2 current is 180° and the 2_1 current and the 2_2 current both are recorded as a second current;
  the $(2k-1)^{th}$ signal generation unit is used for outputting a 2k-1_1 current for the first electrode and a 2k-1_2 current for the second electrode, wherein the frequency of each of the 2k-1_1 current and the 2k-1_2 current is a $(2k-1)^{th}$ frequency value, the phase difference between the 2k-1_1 current and the 2k-1_2 current is 180° and the 2k-1_1 current and the 2k-1_2 current both are recorded as a $(2k-1)^{th}$ current;
  the $2k^{th}$ signal generation unit is used for outputting a 2k_1 current for the third electrode and a 2k_2 current for the fourth electrode, wherein the frequency of each of the 2k_1 current and the 2k_2 current is a $2k^{th}$ frequency value, the phase difference between the 2k_1 current and the 2k_2 current is 180° and the 2k_1 current and the 2k_2 current both are recorded as a $2k^{th}$ current;
  the first frequency value, the second frequency value, the $(2k-1)^{th}$ frequency value and the $2k^{th}$ frequency value all are greater than 1 kHz and are different from one another;
  and the difference between two frequency values of the first frequency value and the second frequency value, . . . , the $(2k-1)^{th}$ frequency value and the $2k^{th}$ frequency value is greater than 1 Hz and is smaller than 100 Hz;
  the first current and the second current are interfered at a deep portion of a brain to form a first focus, and the $(2k-1)^{th}$ current and the $2k^{th}$ current are interfered at the deep portion of the brain to form a $k^{th}$ focus;
  for the first current, the second current, . . . , the $(2k-1)^{th}$ current and the $2k^{th}$ current, each of the currents is a sine wave of which the peak-to-peak value is unchanged all the time; and
  from the first focus to the $k^{th}$ focus, the interference of the currents is not occurred therebetween.

For the above-mentioned embodiment:

(1) Since the brain stimulation system is provided with the k focuses and the k is the positive integer greater than or equal to 2, the brain stimulation system is at least provided with two focuses. When k=3, three focuses may be provided. It should be understood that the focuses are focuses for brain stimulation.

(2) In addition, the phase difference between the foregoing currents is 180°, which is intended to guarantee that a flowing path of the current is between two electrodes, e.g., between the first electrode and the second electrode, or e.g., between the third electrode and the fourth electrode. In this way, the current cross-talk between different frequencies will not appear, thereby being beneficial to guaranteeing the precision of the focuses.

Figure 1:
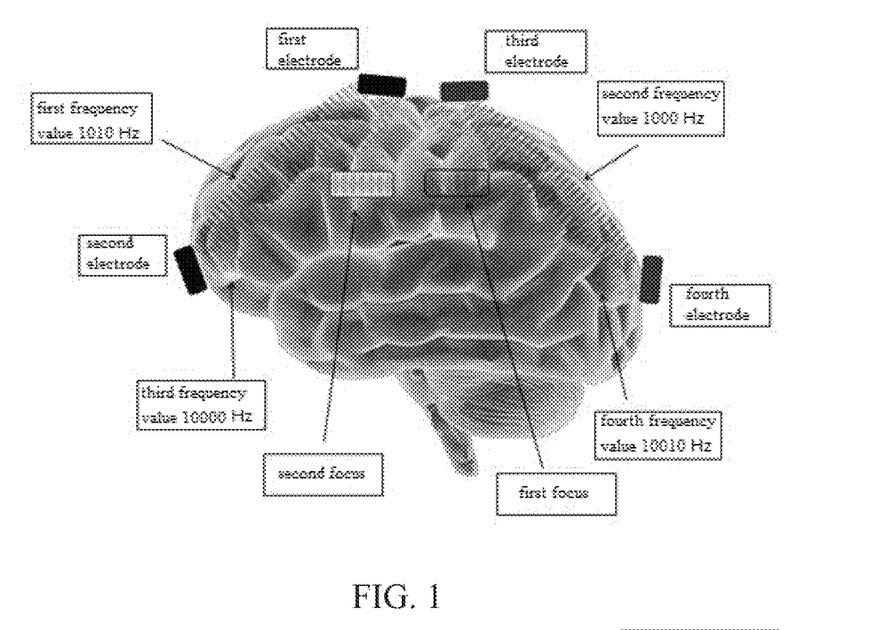
FIG. 1 is a schematic diagram of an embodiment in the present disclosure.

(3) Exemplarily, referring to FIG. 1, the first frequency value corresponding to the first current may be 1010 Hz, the second frequency value corresponding to the second current may be 1000 Hz, the third frequency value corresponding to the third current may be 10000 Hz, and the fourth frequency value corresponding to the fourth current may be 10010 Hz, wherein, it is assumed that the amplitude of the second current is smaller than that of the first current and the amplitude of the third current is smaller than that of the fourth current, and according to a physical principle and the knowledge of interference, the focuses will be close to a side with small amplitude. Therefore, the first focus and the second focus are as shown in the figure, wherein the first focus is close to the side of the second current, and the second focus is close to the side of the third current. For more details about which side the position of each of the focuses is close to, see the description hereinafter.

(4) It should be noted that the above embodiment discloses a brain stimulation system rather than any method for treating or diagnosing a disease. The above-mentioned brain stimulation system may be implemented as a hardware form to be used in a real brain or a simulated brain. Hence, the above embodiment is an object as provided for in Patent Law. More particularly, when being used in simulation, the system may even be implemented as a software form. The brain and the scalp thereof, each of the signal generation units, the currents and the like all may be generated into corresponding models and parameters via software, or even the connection of the electrodes may also be expressed by using a software module.

(5) It should be understood that, the brain stimulation system complies with the object as provided for in Patent Law in itself. If the system is used in noninvasive treatment, the stimulation for the brain deep portion and at least two focuses would be implemented on the premise of non-invasion. The significance lies in that through a noninvasive technology, at least two areas in a brain neural loop (i.e., two nodes in a brain neural network) are stimulated simultaneously to regulate the neural activity of the brain.

The reason why the above-mentioned brain stimulation system has the characteristic of non-invasion is attributed to that the frequency value of each of the currents is beyond 1 kHz and each of the currents is a high-frequency modulation current. Neurons in the brain deep portion have the low-pass filtering characteristic intrinsically, so in the above embodiment (e.g., the first frequency value is 1010 Hz and the second frequency value is 1000 Hz), when the corresponding currents are interfered at the brain deep portion, one first focus is generated. e.g., the frequency difference therebetween is 10 Hz (note: the 10 Hz is greater than 1 Hz and is smaller than 100 Hz in the above embodiment). At this moment, it is apparent that a low-frequency signal is acted on neurons at the first focus. Therefore, the above embodiment implements a noninvasive deep brain stimulation system, in which only the low-frequency signal is acted on the brain deep portion. The third frequency value is 10010 Hz or 10000 Hz and the fourth frequency value may be selected as 10000 Hz or 10010 Hz correspondingly. At this moment, the case is similar and a corresponding low-frequency signal is acted on neurons at the second focus. It should be understood that the first frequency value to the fourth frequency value may also be 2000 Hz, 2010 Hz, 20000 Hz, 20010 Hz and the like sequentially. Generally, the maximum frequency value is not greater than 100000 Hz; and the frequency doubling interference among the currents at different frequency values should be weak as much as possible, thereby being beneficial to precisely positioning the brain deep portion.

(6) If the system is used in simulation, the system can perform simulation on brain stimulation at at least two areas in the same way.

In another embodiment, preferably, the difference ($\Delta f$) between two frequency values of the first frequency value and the second frequency value, ..., the $(2k-1)^{th}$ frequency value and the $2k^{th}$ frequency value is consistent.

It should be understood that this is to prevent the interfered focuses from being interfered again due to the frequency difference to affect the independence of each of the focuses.

In another embodiment,
at any moment, it is assured that the current 1-1 applied on the first electrode and the current 1-2 applied on the second electrode by the first signal generation unit are equal in amplitude and are opposite in direction, so that the current 1-1 flowed out via the first electrode passes through the second electrode completely to flow out in a form of the current 1-2.

In this embodiment, such a case is beneficial for 2 conduction currents controlled by the first signal generation unit (i.e., the current 1-1 and the current 1-2) to flow in strict accordance with set electrode positions and thus a fixed current flowing path is determined.

More preferably, it is also assured that corresponding currents of other signal generation units are equal in amplitude and opposite in direction at any moment.

Therefore, the first signal generation unit, the second signal generation unit, ..., the $(2k-1)^{th}$ signal generation unit and the $2k^{th}$ signal generation unit will respectively and strictly control a flowing path of a stimulation current, so that in a subsequent interference process, the influence among currents output by the signal generation units is reduced, thereby being beneficial to more accurate implementation and positioning of the stimulation focuses.

In another embodiment,
the upper limit of the number k of the focuses is determined by two principles: 1, it is beneficial to suppressing the frequency doubling interference among the currents at different frequency values; and 2, the amplitude of each of the currents is not over-high to damage the brain.

In this case, on one hand, the brain stimulation system can act on multiple focuses and accurately position the brain deep portion within a period of time; and on the other hand, the brain stimulation system is noninvasive to the brain.

In another embodiment,
the amplitude ratio between two of the first current and the second current, ..., the $(2k-1)^{th}$ current and the $2k^{th}$ current is 1:1 to 1:6.

In this embodiment, by flexibly setting the amplitude ratio between two of the first current and the second current, ..., the $(2k-1)^{th}$ current and the $2k^{th}$ current, it is implemented that a position of a corresponding stimulation focus at the brain deep portion is adjusted without changing positions of the multiple electrodes. This is because, in modulation current interference, when the amplitudes or the amplitude ratio of two interfering currents are adjusted, spatial positions where the two currents are interfered are changed. As a result, the larger the amplitude difference of the currents, the closer the focuses to the edge of the side with the small amplitude during brain stimulation. On the contrary, the focuses are close to the center of two currents. The amplitude ratio of 2 conduction stimulation channels formed by the first current and the second current that are interfered to each other to generate the focus determines a position where a target site is located; and by adjusting the currents, the stimulation focus is fallen into a brain area of the target site.

In another embodiment,
each of the signal generation units includes a chip supporting Direct Digital Frequency Synthesis (DDS), so as to implement a sine wave with controllable frequency and phase via one chip.

As mentioned above, it should be understood that since a corresponding chip is adopted, the brain stimulation system at this moment is a system composed of real hardware. This embodiment is to perform model selection on a key component of each signal generation unit in the brain stimulation system of the present disclosure, so as to improve the integration level of the system.

It should be noted that each of the signal generation units may include a respective processor, and may also be connected to a same processor.

In another embodiment,
each of the signal generation units includes: an operational amplifier having a rail to rail characteristic, a wide bandwidth and an optimal working frequency up to an MHz level, so as to implement the following currents at a kHz level via the operational amplifier: the first current and the second current, . . . , the $(2k-1)^{th}$ current and the $2k^{th}$ current.

It should be understood that this embodiment is to perform the model selection on the operational amplifier adopted by the brain stimulation system.

In another embodiment,
a rechargeable battery is adopted by the system to be taken as a power supply.

In this embodiment, with the rechargeable battery, the convenience of the brain stimulation system is improved.

In another embodiment,
each of the signal generation units includes a group of positive and negative power supplies; and a voltage supply range of each of the positive and negative power supplies is subject to an amplitude requirement of the following currents: the first current and the second current, . . . , the $(2k-1)^{th}$ current and the $2k^{th}$ current.

In this embodiment, when each of the signal generation units includes one group of positive and negative power supplies, it is beneficial to independently supplying a power to each of the signal generation units first and then is beneficial to generating two paths of currents at a phase difference of 180° quickly and independently. Therefore, the stability of the system is improved.

In another embodiment,
the system includes a frequency setting unit and/or an amplitude setting unit; the frequency setting unit is used for setting the frequency of each of the following currents: the first current and the second current, . . . , the $(2k-1)^{th}$ current and the $2k^{th}$ current; and
the amplitude setting unit is used for setting the amplitudes or the amplitude ratios of the following currents: the first current and the second current, . . . , the $(2k-1)^{th}$ current and the $2k^{th}$ current.

Apparently, what continues to the technical contributions of the present disclosure is that this embodiment further discloses a frequency setting function, and/or an amplitude setting function. It should be understood that multiple frequency setting units and/or amplitude setting units may be provided, e.g., in one-to-one correspondence with the first signal generation unit to the $2k^{th}$ signal generation unit. It may also be appropriate that the frequency setting and/or amplitude setting functions of all the signal generation units are accomplished via one unit. In a case when the frequency setting units and/or amplitude setting units are in one-to-one correspondence with the first signal generation unit to the $2k^{th}$ signal generation unit, although the cost is improved, it is beneficial to the maintenance and stability of the system.

In another embodiment,
the system comprises a user interface; and the user interface is used for: setting the frequency of each of the foregoing currents, as well as the amplitude or the amplitude ratio; and is used for collecting, in system operation, the parameters of each of the foregoing currents and the loop impedance corresponding to the value of each of the currents in a current state in real time.

In this embodiment, the user interface may be of a hardware type (e.g., various items are set by a hardware-type operation panel) and may also be of a software type (e.g., an application program is operated via a software-type UI interface). As mentioned above, under a more extreme condition, the brain stimulation system may be a system purely composed of a software module and used in simulation. During simulation, the system may be fully used in various scientific researches; and at this moment, the electrodes, the brain and the scalp may be corresponding software modules.

In another embodiment,
the system includes a cascading interface to implement cascading among multiple systems.

It is important to note that the brain stimulation system may be connected with the first signal generation unit, the second signal generation unit . . . one by one via the cascading interface. Hence, the cascading interface is equivalent to a Hub and the brain stimulation system has very good extensibility. At this moment, it may be appropriate to only provide a master power interface on a carrier of the cascading interface, so that power is provided for each of the signal generation units via the master power interface.

In another embodiment,
for the frequency or the amplitude of each of the foregoing currents or the amplitude ratio between two of the first current and the second current, . . . , the $(2k-1)^{th}$ current and the $2k^{th}$ current, corresponding initial setting parameters of the three types of parameters of the frequency, the amplitude, and the amplitude ratio are obtained by simulation in advance.

It should be understood that the frequency is one type of parameter, the amplitude is also one type of parameter and the amplitude ratio is also one type of parameter. For the three types of parameters, the respective corresponding initial settings may be collected along with the work of the brain stimulation system. However, it may also be appropriate to employ a more effective manner: simulation. More particularly, various brains may be modeled, e.g., human brains or other animal brains are modeled massively via the help of volunteers and donations. After the brain is modeled and is simulated, the system implemented by the hardware module may be used for simulation to obtain the above initial settings, and the system implemented by the software module may also be used for simulation to obtain the above initial settings. In addition, when the brain is modeled, a head model of a receptor may employ a cylindrical tissue model, a simple spherical head model, a complex multi-layer spherical head model and a simulation head model constructed based on an MRI image. Typically, after analysis and comparison of the frequency differences and the amplitude ratios between different currents as well as the influences of different positions where the electrodes are connected with the scalp to the stimulation effect (note: electric intensity distributions at focuses), a set of current parameters (e.g., including the frequency, the amplitude and the amplitude ratio, etc.) with the best stimulation performance and an electrode configuration manner may be obtained, thereby guiding the simulation and guiding actual measurement and a future clinical application. In other words, to say the least, through the present disclosure, the stimulation effects of different conditions may be determined according to a simulation result, the stimulation parameters are optimized and the focal change of multi-electrode stimulation is explored.

In another embodiment,
the brain stimulation system is provided with dual focuses for example. When being implemented as the hardware system, the brain stimulation system includes a cascading interface, a battery power supply, a system power button, a voltage-boosting module, a high voltage stabilizing module, a voltage inversion module, a microprocessor connected with the system power button via a low voltage stabilizing module, a partial voltage setting button and a frequency setting button connected with an input end of the microprocessor, and a system display module, a first signal generation module and a second signal generation module connected with an output end of the microprocessor, wherein an output end of the first signal generation module is respectively connected with a first current modulation module and a second current modulation current;

an output end of the second signal generation module is respectively connected with a third current modulation module and a fourth current modulation module; and output ends of the high voltage stabilizing module and the voltage inversion module are respectively connected with the four current modulation modules.

When electrodes include a first electrode to a fourth electrode, the first current modulation module to the fourth current modulation module are respectively connected to the electrode output interfaces to output stimulation currents, wherein the electrode output interface connected with the first current modulation module and the electrode output interface connected with the second current modulation module output sinusoidal stimulation currents that are same in frequency and amplitude and opposite in phase, and the electrode output interface connected with the third current modulation module and the electrode output interface connected with the fourth current modulation module output sinusoidal stimulation currents that are same in frequency and amplitude and opposite in phase; and all the current frequencies, phases and amplitudes may be set via the partial pressure setting button and the frequency setting button.

In this way, for four electrodes connected to two sides of the scalp, 2 conduction simulation currents are respectively added to each electrode and every 2 conduction simulation currents generate 1 conduction stimulation channel, and thus 4 conduction stimulation channels are generated in total. Every 2 conduction stimulation channels generate an interference focus and two stimulation focuses are generated in total.

It should be understood that the voltage-boosting module provides an enough voltage source for the subsequent constant current circuit; and the significance of the related voltage stabilizing module lies in that if a battery is adopted to supply the power, the voltage amplitude output by the voltage-boosting module changes along with an output voltage of the power supply battery, and the voltage stabilizing module may remove this flotation to provide a stable voltage source for the constant current circuit.

More preferably, each of the current modulation modules includes a direct-current removal module, a voltage-dividing module, a constant current module and the electrode output interface that are connected in sequence; output ends of the signal generation modules are connected to input ends of the direct-current removal modules; and output ends of the high voltage stabilizing module and the voltage inversion module are respectively connected to a power input end of each of the constant current modules.

Figure 2:
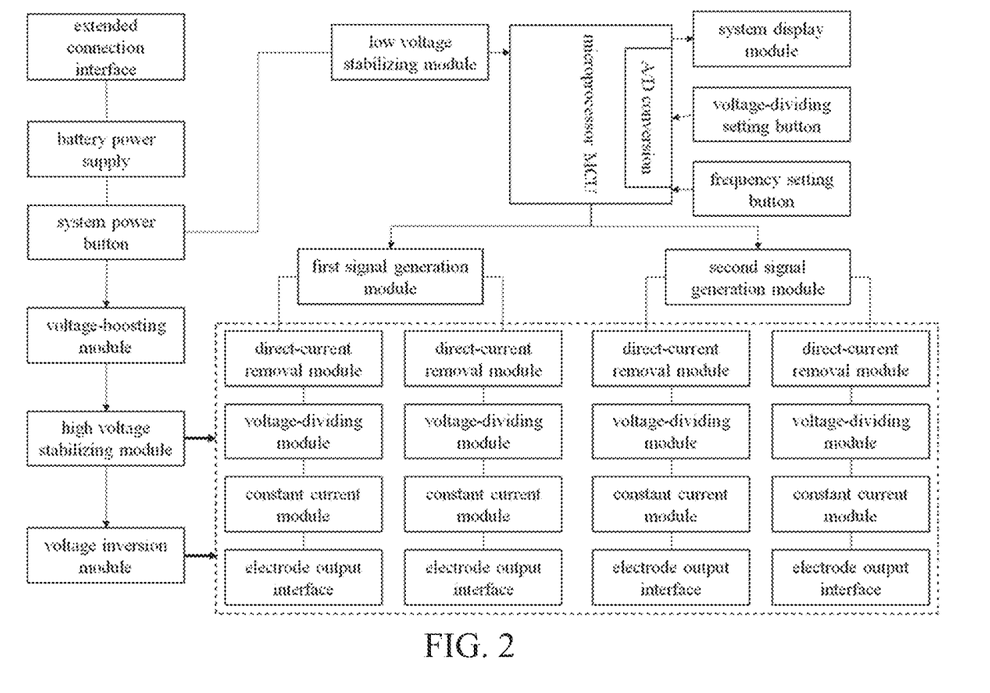
FIG. 2 is a schematic diagram of a circuit structure of an embodiment in the present disclosure.

Referring to FIG. 2, the system is powered by a 9V nickel-hydrogen rechargeable battery and the power is supplied to the microprocessor (e.g., an MCU) via the voltage stabilizing module, wherein, an A/D conversion module is used for calculating a current amplitude and a load resistance of the system. The microprocessor (e.g., the MCU) is connected with an external voltage-dividing setting button and the like, wherein the voltage-dividing setting button may be used for setting the current amplitude and a frequency setting button may be used for setting a current frequency. The system display module displays the current amplitude, frequency, load impedance, and stimulation time during stimulation. The microprocessor writes stimulation information into the signal generation modules via a communication interface, the signal generation modules provide a stimulation signal source for a stimulation circuit and the stimulation signal source is finally output to the electrode output interfaces via the direct-current removal modules, voltage-dividing modules and constant current modules. Besides, the voltage of the power supply battery provides positive and negative power supplies for the stimulation circuit via the voltage-boosting module, the voltage stabilizing module and the voltage inversion module.

Figure 3:
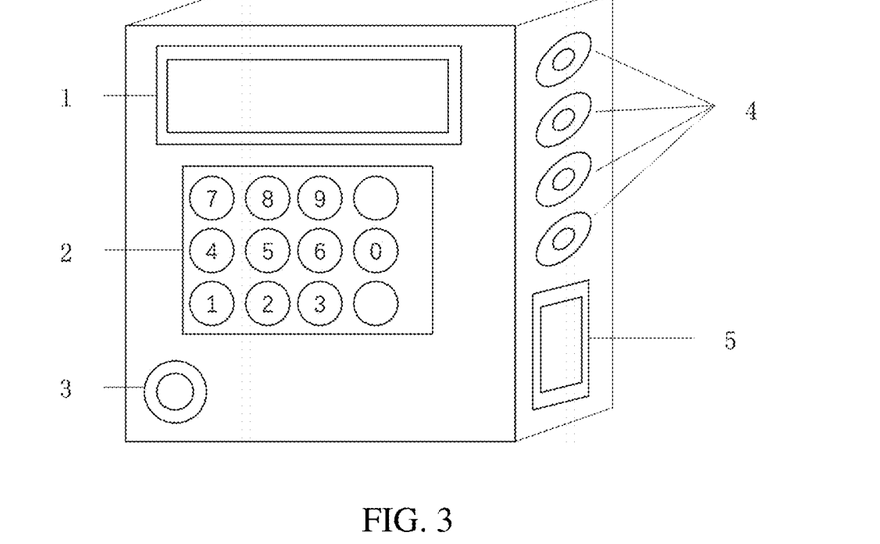
FIG. 3 is a schematic diagram of a circuit appearance of an embodiment in the present disclosure.

Referring to FIG. 3, after the extended connection interface 5 (i.e., an implementation manner of the cascading interface) is connected, the system power button 3 may be clicked by a user, stimulation parameters are set via the parameter setting buttons 2 and the stimulation electrodes are connected to the electrode output interfaces 4. When the system works, the system display screen 1 displays the system measured stimulation current amplitude, frequency, load impedance, and stimulation time. The extended connection interface 5 is used for implementing connection among multiple systems to form a set of overall stimulation system.

Figure 4:
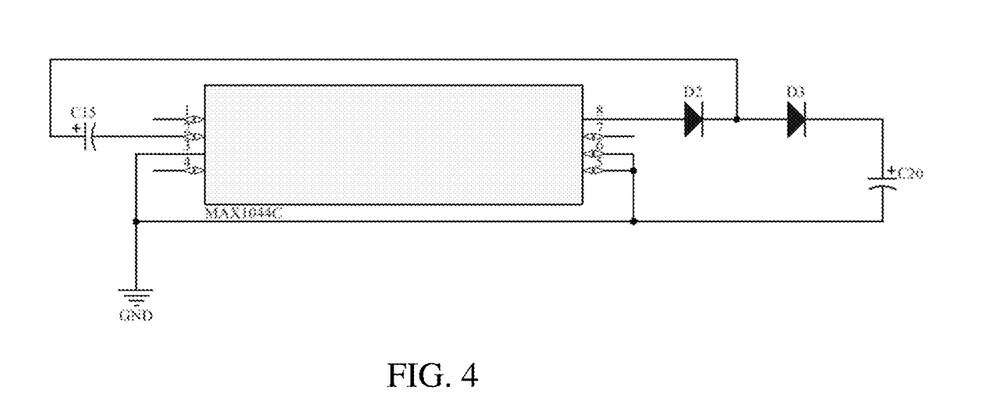
FIG. 4 is a circuit diagram of a voltage-boosting module of an embodiment in the present disclosure.

Referring to FIG. 4, the voltage-boosting module includes a voltage-boosting chip MAX1044, a diode D2, a diode D3, a capacitor C20 and a capacitor C15; the positive electrode of the diode D2 is connected to a pin 8 of the voltage-boosting chip MAX1044, and the negative electrode of the diode D2 is connected to the positive electrode of the diode D3 and the positive electrode of the capacitor C20; the negative electrode of the diode D3 is connected to the positive electrode of the capacitor C15; the negative electrode of the capacitor C20 is connected to a pin 3 of the MAX1044 and the ground, the negative electrode of the capacitor C15 is connected to a pin 2 of the MAX1044, a pin 5 and a pin 6 of the MAX1044 are grounded, the pin 8 of the MAX1044 is connected to the system power button and the rest pins are suspended.

Figure 5:
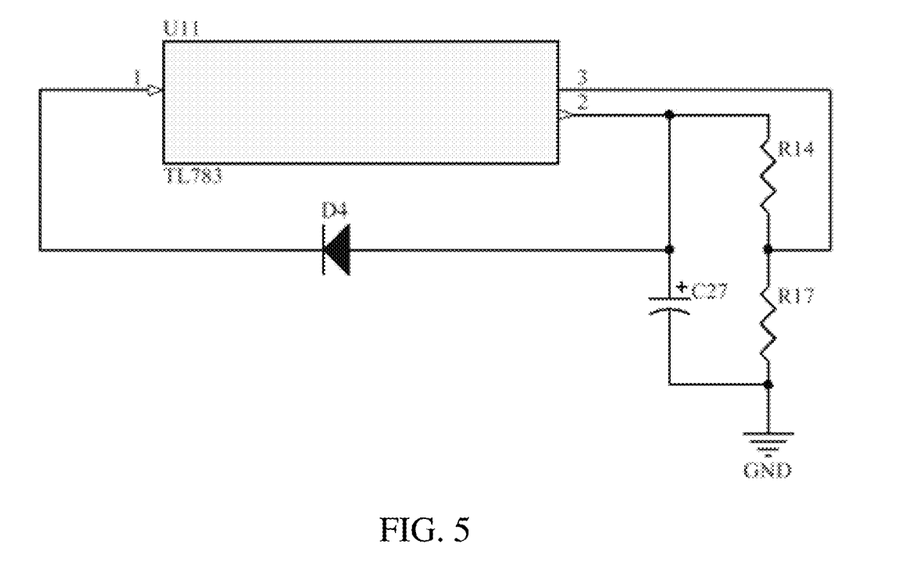
FIG. 5 is a circuit diagram of a high voltage stabilizing module of an embodiment in the present disclosure.

Referring to FIG. 5, the high voltage stabilizing module includes a voltage stabilizing chip TL783, a diode D4, a capacitor C27, a resistor R17 and a resistor R14; the positive electrode of the diode D4 is connected to the positive electrode of the capacitor C27, one end of the resistor R14 and a pin 2 of the voltage stabilizing chip TL783, the negative electrode of the diode D4 is connected to a pin 1 of the voltage stabilizing chip TL783, one end of the resistor R17 is connected to the other end of the resistor R14 and a pin 3 of the voltage stabilizing chip TL783, the other end of the resistor R17 is connected to the negative electrode of the capacitor C27 and the ground, and the pin 1 of the voltage stabilizing chip TL783 is connected to the positive electrode of the capacitor C20.

Figure 6:
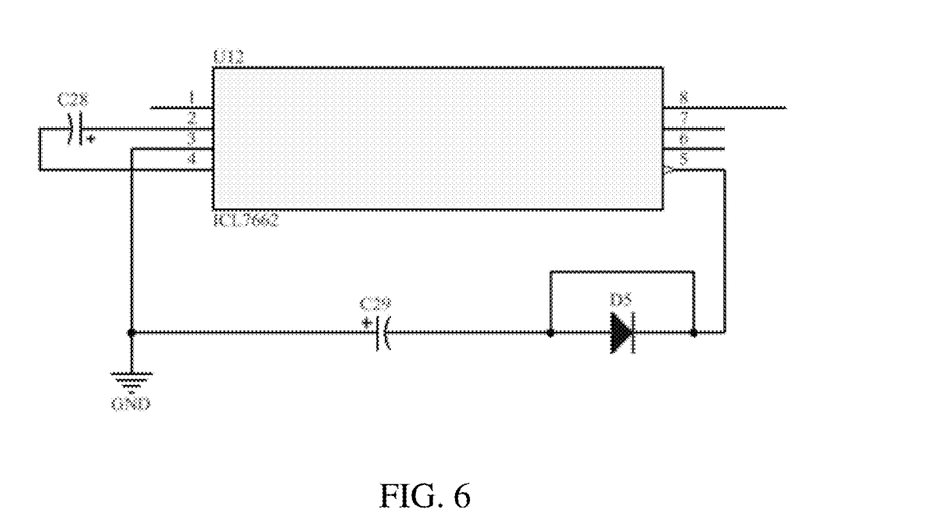
FIG. 6 is a circuit diagram of a voltage inversion module of an embodiment in the present disclosure.

Referring to FIG. 6, the voltage inversion module includes a voltage inversion chip ICL7662, a capacitor C28, a capacitor C29 and a diode D5; the positive electrode of the capacitor C28 is connected to a pin 2 of the voltage inversion chip ICL7662, the negative electrode of the capacitor C28 is connected to a pin 4 of the voltage inversion chip ICL7662, the positive electrode of the capacitor C29 is connected to a pin 3 of the voltage inversion chip ICL7662 and the ground, the negative electrode of the capacitor C29 is connected to the positive electrode and the negative electrode of the diode D5, the negative electrode of the diode D5 is connected to a pin 5 of the voltage inversion chip ICL7662 and a pin 8 of the voltage inversion chip ICL7662 is connected to the pin 2 of the voltage stabilizing chip TL783.

Figure 7:
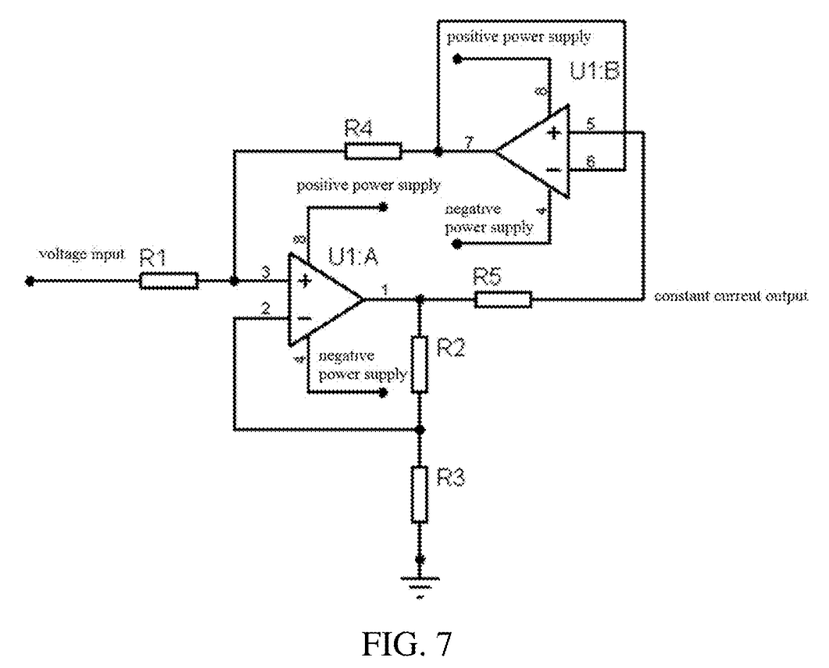
FIG. 7 is a circuit diagram of a constant current module of an embodiment in the present disclosure.

Referring to FIG. 7, the constant current module includes a high-voltage high-frequency operational amplification chip; a voltage input is flowed to a pin 3 of the operational amplification chip via a resistor R1, a pin 1 is connected to one end of a resistor R5 and one end of a resistor R2, a pin 2 is connected to the other end of the resistor R2 and one end of a resistor R3, a pin 3 is connected to one end of the resistor R1 and one end of a resistor R4, a pin 4 is connected to a negative power supply, a pin 5 is connected to the other end of the resistor R5 and is taken as an output end of a constant current, a pin 7 is connected to the other end of the resistor R4 and a pin 6, and a pin 8 is connected to a positive power supply.

More particularly, the constant current module includes an operational amplifier U1:A, an operational amplifier U1:B, and resistors R1 to R5; a voltage input is connected to one end of the resistor R1, the other end of the resistor R1 is respectively connected to one end of the resistor R4 and the positive input end of the operational amplifier U1:A, one end of the resistor R2 is connected to the negative input end of the operational amplifier U1:A and one end of the resistor R3, the other end of the resistor R2 is connected to the output end of the operational amplifier U1:A and one end of the resistor R5, the other end of the resistor R3 is grounded, the other end of the resistor R4 is connected to the output end and the negative input end of the operational amplifier U1:B, and the other end of the resistor R5 is respectively connected to the positive input end of the operational amplifier U1:B and the electrode output interface.

More preferably, a circuit relevant to the constant current module is intended to generate a positive amplitude current and a negative amplitude current, or a phase difference of 180°. As a result, when the circuit is powered, it preferably not only includes a positive voltage source, but also includes a negative voltage source, and the voltage inversion module provides a stable negative voltage source for the circuit relevant to the constant current module.

Further, the transcranial noninvasive deep brain dual-focus stimulation method for a neural loop provided by the present disclosure includes the following steps:
1) a personalized head model stimulation and simulation system is established;
2) extended connection interfaces and power supply batteries of two interface extendable transcranial noninvasive deep brain dual-focus stimulation apparatuses are connected and the transcranial noninvasive deep brain dual-focus stimulation apparatus is constructed;
3) optimized stimulation parameters are determined according to a simulation result; the output of the first stimulation apparatus is as follows: output currents of the electrode output interface connected with the first current modulation module and the electrode output interface connected with the second current modulation module are respectively output at 1.6 mA/1 KHz, and output currents of the electrode output interface connected with the third current modulation module and the electrode output interface connected with the fourth current modulation module are respectively output at 0.4 mA/1.01 KHz; the output of the second stimulation apparatus is as follows: output currents of the electrode output interface connected with the first current modulation module and the electrode output interface connected with the second current modulation module are respectively output at 1.6 mA/10 KHz, and output currents of the electrode output interface connected with the third current modulation module and the electrode output interface connected with the fourth current modulation module are respectively output at 0.4 mA/10.01 KHz, wherein the electrode output interface connected with the first current modulation module and the electrode output interface of the second current modulation module in the first stimulation apparatus as well as the electrode output interface connected with the third current modulation module and the electrode output interface connected with the fourth current modulation module in the second stimulation apparatus are connected to a same side of a brain; and meanwhile, the above current frequencies are kept unchanged, ratios of the output currents of the electrode output interface connected with the first current modulation module and the electrode output interface of the second current modulation module to the output currents of the electrode output interface connected with the third current modulation module and the electrode output interface connected with the fourth current modulation module are adjusted, different positions of a stimulation target site are adjusted and the ratios of the output currents of the two apparatuses are adjusted simultaneously and are consistent;
4) the system power button is closed, and after the system is started, the MCU and the stimulation circuit are initialized;
5) a stimulation electrode is connected to one electrode output interface, and a stimulation site is selected;
6) the stimulation electrode is attached to the stimulation site selected on a scalp;
7) the amplitude and frequency of a stimulation current are set according to a simulation result, and a button is clicked to write into a stimulation signal; and
8) the system starts to stimulate, data are collected via the A/D conversion module and a timing module, the stimulation current amplitude, stimulation current frequency, load impedance and stimulation time are displayed on the system display screen, and after the stimulation time is reached, the stimulation is ended.

To sum up, the above embodiments are merely used for illustrating the technical solutions of the present disclosure, rather than limiting the present disclosure; although the present disclosure is illustrated in detail with reference to the aforementioned embodiments, it should be understood by a person skilled in the art that modifications may still be made on the technical solutions disclosed in the aforementioned respective embodiments, or equivalent substitutions may be made to part of the technical characteristics thereof; and these modifications or substitutions do not make the nature of the corresponding technical solutions depart from the spirit and scope of the technical solutions of the respective embodiments of the present disclosure.

What is claimed is:

1. A deep brain stimulation system having k focuses, comprising:
   a first electrode and a second electrode, used for connecting one side of a scalp of a brain;
   a third electrode and a fourth electrode, used for connecting another side of the scalp;
   a microprocessor;
   a high voltage stabilizing module;
   a voltage inversion module; and
   a first signal generation unit, a second signal generation unit, up to a $(2k-1)^{th}$ signal generation unit and a $2k^{th}$ signal generation unit, wherein the k is a positive integer greater than or equal to 2;

the first signal generation unit is used for outputting a first current of the first signal generation unit for the first electrode and a second current of the first signal generation unit for the second electrode, wherein the frequency of each of the first current of the first signal generation unit and the second current of the first signal generation unit is a first frequency value, the phase difference between the first current and the second current of the first signal generation unit is 180° and the first current of the first signal generation unit and the second current of the first signal generation unit both are recorded as a first interference current;

the second signal generation unit is used for outputting a first current of the second signal generation unit for the third electrode and a second current of the second signal generation unit for the fourth electrode, wherein the frequency of each of the first current and the second current of the second signal generation unit is a second frequency value, the phase difference between the first current and the second current of the second signal generation unit is 180° and the first current and the second current of the second signal generation unit both are recorded as a second interference current;

the $(2k-1)^{th}$ signal generation unit is used for outputting a first current of the $(2k-1)^{th}$ signal generation unit for the first electrode and a second current of the $(2k-1)^{th}$ signal generation unit for the second electrode, wherein the frequency of each of the first current and the second current of the $(2k-1)^{th}$ signal generation unit is a $(2k-1)^{th}$ frequency value, the phase difference between the first current and the second current of the $(2k-1)^{th}$ signal generation unit is 180° and the first current and the second current of the $(2k-1)^{th}$ signal generation unit both are recorded as a $(2k-1)^{th}$ interference current;

the $2k^{th}$ signal generation unit is used for outputting a first current of the $2k^{th}$ signal generation unit for the third electrode and a second current of the $2k^{th}$ signal generation unit for the fourth electrode, wherein the frequency of each of the first current of the $2k^{th}$ signal generation unit and the second current of the $2k^{th}$ signal generation unit is a $2k^{th}$ frequency value, the phase difference between the first current and the second current is 180° and the first current and the second current both are recorded as a $2k^{th}$ interference current;

the first frequency value, the second frequency value, the $(2k-1)^{th}$ frequency value and the $2k^{th}$ frequency value all are greater than 1 kHz and are different from one another; and the difference between two frequency values of the first frequency value and the second frequency value, up to the $(2k-1)^{th}$ frequency value and the $2k^{th}$ frequency value is greater than 1 Hz and is smaller than 100 Hz;

the microprocessor is configured that the first interference current and the second interference current are interfered at a deep portion of a brain to form a first focus, and the $(2k-1)^{th}$ current and the $2k^{th}$ current are interfered at the deep portion of the brain to form a $k^{th}$ focus;

the microprocessor is further configured that for the first interference current, the second interference current, up to the $(2k-1)^{th}$ interference current and the $2k^{th}$ interference current, each of the interference currents is a sine wave of which the peak-to-peak value is unchanged all the time;

the microprocessor is still further configured that from the first focus to the $k^{th}$ focus, the interference of the interference currents is not occurred therebetween, wherein the first interference current and the second interference current responsible for the first focus do not intersect with the $(2k-1)^{th}$ interference current and the $2k^{th}$ interference current responsible for the $k^{th}$ focus;

the first signal generation module and the second signal generation module are connected to an output end of the microprocessor, wherein an output end of the first signal generation module is respectively connected with a first current modulation module and a second current modulation module;

an output end of the second signal generation module is respectively connected to a third current modulation module and a fourth current modulation module; and output ends of the high voltage stabilizing module and the voltage inversion module are respectively connected to the four current modulation modules.

2. The system of claim 1, wherein
each of the signal generation units comprises a chip supporting Direct Digital Frequency Synthesis (DDS), so as to implement a sine wave with controllable frequency and phase via one chip.

3. The system of claim 1, wherein
each of the signal generation units comprises: an operational amplifier having a rail to rail characteristic, a bandwidth and a working frequency up to an MHz level, so as to implement the following currents at a kHz level via the operational amplifier: the first interference current and the second interference current, up to the $(2k-1)^{th}$ interference current and the $2k^{th}$ interference current.

4. The system of claim 1, wherein the system further comprises a rechargeable battery and the rechargeable battery is adopted by the system to be taken as a power supply.

5. The system of claim 1, wherein
each of the signal generation units comprises a group of positive and negative power supplies; and a voltage supply range of each of the positive and negative power supplies is subject to an amplitude requirement of the following currents: the first interference current and the second interference current, up to the $(2k-1)^{th}$ interference current and the $2k^{th}$ interference current.

6. The system of claim 1, wherein
the system comprises a frequency setting unit and/or an amplitude setting unit;
the frequency setting unit is used for setting the frequencies of the following currents: the first interference current and the second interference current, up to the $(2k-1)^{th}$ interference current and the $2k^{th}$ interference current; and
the amplitude setting unit is used for setting the amplitudes or the amplitude ratios of the following currents: the first interference current and the second interference current, up to the $(2k-1)^{th}$ interference current and the $2k^{th}$ interference current.

7. The system of claim 1, wherein
the system comprises a user interface; and the user interface is used for setting the frequency of each of the foregoing currents, as well as the amplitude or the amplitude ratio; and is used for collecting, in system operation, the parameters of each of the foregoing currents and the loop impedance corresponding to the value of each of the currents in a current state in real time.

8. The system of claim 1, wherein
the system comprises a cascading interface to implement cascading among multiple systems.

9. The system of claim 1, wherein
for the frequency or the amplitude of each of the foregoing currents or the amplitude ratio between two of the first interference current and the second interference current, up to the $(2k-1)^{th}$ interference current and the $2k^{th}$ interference current, corresponding initial setting parameters of the three types of parameters of the frequency, the amplitude, and the amplitude ratio are obtained by simulation in advance.

10. The system of claim 1, wherein the high voltage stabilizing module comprises a voltage stabilizing chip, a first diode, a first capacitor, a first resistor and a second resistor; the positive electrode of the first diode is connected to the positive electrode of the first capacitor, one end of the second resistor and a pin of the voltage stabilizing chip, the negative electrode of the first diode is connected to a pin 1 of the voltage stabilizing chip, one end of the second resistor is connected to the other end of the second resistor and a pin 3 of the voltage stabilizing chip, the other end of the first resistor is connected to the negative electrode of the first capacitor and the ground, and the pin 1 of the voltage stabilizing chip is connected to the positive electrode of the first capacitor.

11. The system of claim 10, wherein the voltage inversion module comprise a voltage inversion chip, a second capacitor, a third capacitor and a second diode; the positive electrode of the second capacitor is connected to a pin 2 of the voltage inversion chip, the negative electrode of the second capacitor is connected to a pin 4 of the voltage inversion chip, the positive electrode of the third capacitor is connected to a pin 3 of the voltage inversion chip and the ground, the negative electrode of the third capacitor is connected to the positive electrode and the negative electrode of the second diode, the negative electrode of the second diode is connected to a pin 5 of the voltage inversion chip and a pin 8 of the voltage inversion chip is connected to the pin 2 of the voltage stabilizing chip.

12. The system of claim 11, wherein each of the first, second, third and fourth current modulation modules includes a direct-current removal module, a voltage-dividing module, a constant current module, and the electrode output interface that are connected in sequence.

* * * * *